United States Patent
Dell

(10) Patent No.: US 8,932,351 B2
(45) Date of Patent: Jan. 13, 2015

(54) ACCOMMODATIVE INTRAOCULAR LENS HAVING A HAPTIC PLATE

(75) Inventor: Steven J. Dell, Austin, TX (US)

(73) Assignee: Steven J. Dell, Austin, TX (US)

( * ) Notice: Subject to any disclaimer, the term of this patent is extended or adjusted under 35 U.S.C. 154(b) by 1173 days.

(21) Appl. No.: 12/129,379

(22) Filed: May 29, 2008

(65) Prior Publication Data

US 2009/0248154 A1 Oct. 1, 2009

Related U.S. Application Data

(60) Provisional application No. 60/932,079, filed on May 29, 2007.

(51) Int. Cl.
*A61F 2/16* (2006.01)

(52) U.S. Cl.
CPC ............. *A61F 2/1624* (2013.01); *A61F 2/1613* (2013.01); *A61F 2/1629* (2013.01); *A61F 2002/1689* (2013.01); *A61F 2250/0018* (2013.01)
USPC .......................... 623/6.46; 623/6.44; 623/6.4

(58) Field of Classification Search
USPC ............................. 623/6.38–6.44, 6.46, 6.49
See application file for complete search history.

(56) References Cited

U.S. PATENT DOCUMENTS

| | | | |
|---|---|---|---|
| 4,122,556 A | 10/1978 | Poler | |
| 4,315,337 A | * 2/1982 | Choyce | 623/6.43 |
| 4,872,876 A | * 10/1989 | Smith | 623/6.44 |
| 4,878,911 A | 11/1989 | Anis | |
| 4,878,912 A | 11/1989 | Castleman | |
| 6,302,911 B1 | 10/2001 | Hanna | |
| 6,423,094 B1 | 7/2002 | Sarfarazi | |
| 6,488,708 B2 | 12/2002 | Sarfarazi | |
| 6,596,006 B1 | 7/2003 | Hanna | |
| 6,740,116 B2 | 5/2004 | Morcher | |
| 6,749,634 B2 | 6/2004 | Hanna | |
| 6,761,737 B2 | 7/2004 | Zadno-Azizi et al. | |
| 6,849,091 B1 | 2/2005 | Cumming | |
| 7,217,112 B2 | 5/2007 | Kyburz et al. | |
| 7,226,479 B2 | 6/2007 | MeBner et al. | |
| 7,238,201 B2 | 7/2007 | Portney et al. | |
| 7,384,429 B2 | 6/2008 | Hanna | |

(Continued)

FOREIGN PATENT DOCUMENTS

| | | |
|---|---|---|
| EP | 0024126 A1 | 2/1981 |
| EP | 0993281 B1 | 2/2004 |

(Continued)

OTHER PUBLICATIONS

European Communication in corresponding EP Application No. 12 170 455.5 dated May 9, 2014 (4 pages).

*Primary Examiner* — David H Willse
*Assistant Examiner* — Tiffany Shipmon
(74) *Attorney, Agent, or Firm* — Toan P. Vo

(57) ABSTRACT

An accommodating intraocular lens (AIOL) comprising an optic, and at least one haptic plate coupled to the optic by at least one connector, the connector being less rigid than the haptic plate, the at least one haptic plate surrounding the optic, and the optic and haptic plate having a combined surface area between 70 mm$^2$ and 100 mm$^2$. The at least one haptic plate may form a continuous 360-degree boundary around the optic. The at least one haptic plate has a width in a radial dimension of 1.0-3.5 mm across its entire angular extent.

4 Claims, 6 Drawing Sheets

(56) References Cited

U.S. PATENT DOCUMENTS

| | | |
|---|---|---|
| 2003/0130732 A1 | 7/2003 | Sarfarazi |
| 2003/0135272 A1* | 7/2003 | Brady et al. ............... 623/6.37 |
| 2004/0015236 A1 | 1/2004 | Sarfarazi |
| 2005/0015144 A1 | 1/2005 | Tran |
| 2005/0125057 A1 | 6/2005 | Cumming |
| 2005/0125058 A1 | 6/2005 | Cumming et al. |
| 2005/0234547 A1 | 10/2005 | Nguyen et al. |
| 2005/0267575 A1 | 12/2005 | Nguyen et al. |
| 2006/0020339 A1* | 1/2006 | Ran ............... 623/6.37 |
| 2006/0064161 A1* | 3/2006 | Blake ............... 623/6.37 |
| 2006/0259140 A1 | 11/2006 | Dell |
| 2007/0198084 A1 | 8/2007 | Cumming et al. |
| 2007/0260309 A1 | 11/2007 | Richardson |
| 2007/0260310 A1 | 11/2007 | Richardson |
| 2008/0021550 A1* | 1/2008 | Richardson ............... 623/6.37 |
| 2008/0027539 A1 | 1/2008 | Cumming |
| 2008/0154364 A1 | 6/2008 | Richardson et al. |

FOREIGN PATENT DOCUMENTS

| | | |
|---|---|---|
| WO | 99/29266 A1 | 6/1999 |
| WO | WO 00/21467 A1 | 4/2000 |
| WO | WO 02/056758 A1 | 7/2002 |
| WO | WO 03/015668 A1 | 2/2003 |
| WO | WO 03/044946 A2 | 5/2003 |
| WO | WO 2004/012631 A1 | 2/2004 |
| WO | WO 2004/024043 A2 | 3/2004 |
| WO | WO 2005/115278 A1 | 12/2005 |
| WO | WO 2006/040041 A1 | 4/2006 |

* cited by examiner

ACCOMMODATIVE INTRAOCULAR LENS HAVING A HAPTIC PLATE

CROSS-REFERENCE

This application claims benefit of U.S. Provisional Application 60/932,079, titled VITREOUS PRESSURE CONCENTRATING ACCOMMODATING INTRAOCULAR LENS, filed May 29, 2007, by Steven Dell, which is hereby incorporated by reference.

FIELD OF INVENTION

The present invention relates to accommodative intraocular lenses (AIOLs), and more particularly to AIOLs having a haptic plate surrounding an optic.

BACKGROUND OF THE INVENTION

FIG. 1 illustrates a cross-sectional view of a human eye 10 having an anterior chamber 12 and a posterior chamber 14 separated by an iris 30. Within the posterior chamber 14 is a capsular bag 16 which holds the eye's natural crystalline lens 17. The capsular bag comprises an anterior capsule 16a and a posterior capsule 16b that meet at a capsular rim 16c. Light enters the eye by passing through cornea 18. The cornea and crystalline lens act together to direct and focus the light onto retina 20. The retina is connected to optic nerve 22 which transmits images received by the retina to the brain for interpretation. Eye 10 has a visual axis VA In an eye where the natural crystalline lens has been damaged (e.g., clouded by cataracts), the natural lens is no longer able to properly focus and/or direct incoming light to the retina. As a result images become blurred. A well known surgical technique to remedy this situation involves removal of a damaged crystalline lens through a hole in the capsular bag known as a capsularhexis (also referred to simply as a rhexis). Subsequently, an artificial lens known as an intraocular lens (IOL) can be placed into the evacuated capsular bag through the rhexis.

Conventional IOLs are typically fixed-focus lenses. Such lenses are usually selected to have an optical power such that the patient has a fixed focus for distance vision, and the patient requires spectacles or contact lenses to permit near vision. In recent years extensive research has been carried out to develop IOLs having variable focus capability. Such IOLs are known as accommodating IOLs (AIOLS). The term "AIOLs" refers to both single-element and multi-element systems.

Single-element AIOLs typically have two or more haptics, each comprising a plate to position the lens in the capsular bag and to mechanically interact with the capsular bag to achieve accommodative movement. For example, the haptics extend generally radially outward from sides of the optic and are movable anteriorly and posteriorly relative to the optic.

In some conventional lens embodiments, the plate haptics are hinged proximate the optic to permit anterior/posterior movement of the optic and haptic. The accommodative movement involves pivotal movement of the haptics at their corresponding hinge and translation of the optic relative to the eye; accordingly, the optic and the haptics undergo accommodative movement. In other conventional embodiments, the plate haptics are resiliently flexible, and the anterior/posterior movement of the haptics relative to the optic involves resilient flexing or bending of the haptics throughout their lengths.

Conventional lenses having plate haptics are constructed and arranged to utilize compression of the capsular rim, the elasticity of the posterior capsule and pressure in the vitreous cavity 19, in combination with the natural brain-controlled ciliary muscle action of the eye to provide postoperative accommodation for near vision. Thus, according to some eye models, when looking at a near object, the brain constricts the ciliary muscle thereby relaxing the fibrosed anterior rim and increasing vitreous cavity pressure in such a way as to effect forward movement of the lens, i.e. accommodation movement of the lens optic along the axis of the eye to a near vision position. Depending upon the amount of accommodation, accommodation deflection of the lens is produced initially by an increase in viteous pressure due to backward movement of the ciliarly muscle into the vitreous body as the muscle contracts thereby causing the vitreous body to bulge forward at its boundary with the capsular bag, and a forward bias force of the stretched posterior capsule and finally by forward movement of the lens. Subsequent brain-activated relaxation of the ciliary muscle causes the capsular bag and the fibrosed anterior capsular rim to return the lens rearward toward its distant vision position.

SUMMARY

Aspects of the present invention are the result of observations by the Applicant that the movement of the vitreous body occurs across substantially the entire boundary of the vitreous body that is in proximity to the capsular bag. The Applicant has determined that conventional AIOLs that contact the posterior capsular bag along only a portion of the posterior capsule (e.g., two diametrically opposed haptics) allows the capsular bag to herniate around the lens as vitreous pressure is increased, thereby failing to utilize all movement of the vitreous body that is capable of contributing to accommodative movement of the AIOL. Accordingly, an aspect of the present invention is directed to AIOL constructions in which a haptic plate surrounds an optic on all sides (i.e., 360 degrees) such that the haptics contacts substantially the entirety of the posterior capsular bag.

An aspect of the invention is directed to an accommodating intraocular lens (AIOL) comprising an optic, and at least one haptic plate coupled to the optic by at least one connector. The connector is less rigid than the haptic plate, and the at least one haptic plate surrounds the optic. The optic and haptic plate have a combined surface area between 70 mm$^2$ and 100 mm$^2$.

In some embodiments, the at least one haptic plate forms a continuous 360-degree boundary around the optic. The at least one haptic plate may comprise at least two haptic plates. In some embodiments, the at least one haptic plate has an area of at least 60 mm$^2$.

In some embodiments, the at least one haptic plate has a width in a radial dimension of 1.0-3.5 mm across its entire angular extent. The at least one connector may comprise at least two connectors.

In some embodiments, the at least one haptic plate has a thickness that is greater than the thickness of any portion of the at least one connector. In some embodiments, the at least one haptic plate forms a conical shape. In some embodiments, the AIOL does not have a binge between the optic and the at least one haptic plate.

In some embodiments, the combined surface area is between 75 mm$^2$ and 100 mm$^2$. The combined surface area may be between 80 mm$^2$ and 100 mm$^2$.

Another aspect of the invention is directed to a method of applying an accommodating intraocular lens (AIOL), the method comprising (A.) providing an AIOL comprising (i.) an optic, and (ii.) at least one haptic plate coupled to the optic by at least one connector, the connector being less rigid than the haptic plate, and the at least one haptic plate surrounding the optic, and (B.) implanting the lens into an eye, the at least one haptic plate and optic covering between 65% and 95% of a posterior capsule of the eye. Typically the posterior capsule diameter is in a range from 10-13 mm.

In some embodiments, the at least one haptic plate and optic cover between 70% and 95% of a posterior capsule of the eye. In some embodiments, the at least one haptic plate and optic cover between 75% and 95% of a posterior capsule of the eye. The at least one haptic plate and optic may cover between 80% and 95% of the posterior capsule of the eye.

In some embodiments, the at least one haptic plate forms a continuous 360-degree boundary around the optic. In some embodiments, the at least one haptic plate has a width in the radial dimension of 1.0-3.5 mm across its entire angular extent. In some embodiments, the at least one connector comprises at least two connectors.

Yet another aspect of the invention is directed to an accommodating intraocular lens (AIOL) comprising an optic and at least one haptic plate coupled to the optic by at least one connector. The connector is less rigid than the haptic plate, and the at least one haptic plate surrounds the optic. The at least one haptic plate has a width in a radial dimension of 1.0-3.5 mm across its entire angular extent.

In some embodiments, the at least one haptic plate forms a continuous 360-degree boundary around the optic. The at least one haptic plate may comprise at least two haptic plates. The at least one haptic plate may have an area of at least 60 mm$^2$.

In some embodiments, the optic and haptic plate have a combined surface area between 70 mm$^2$ and 100 mm$^2$. The at least one connector may comprise at least two connectors.

In some embodiments, the at least one haptic plate has a thickness that is greater than the thickness of any portion of the at least one connector. In some embodiments, the at least one haptic plate forms a conical shape. In some embodiments, the AIOL does not have a hinge between the optic and the at least one haptic plate.

In some embodiments, the combined surface area is between 75 mm$^2$ and 100 mm$^2$. The combined surface area may be between 80 mm$^2$ and 100 mm$^2$. The haptic plate may be hingeless.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Figure 1:
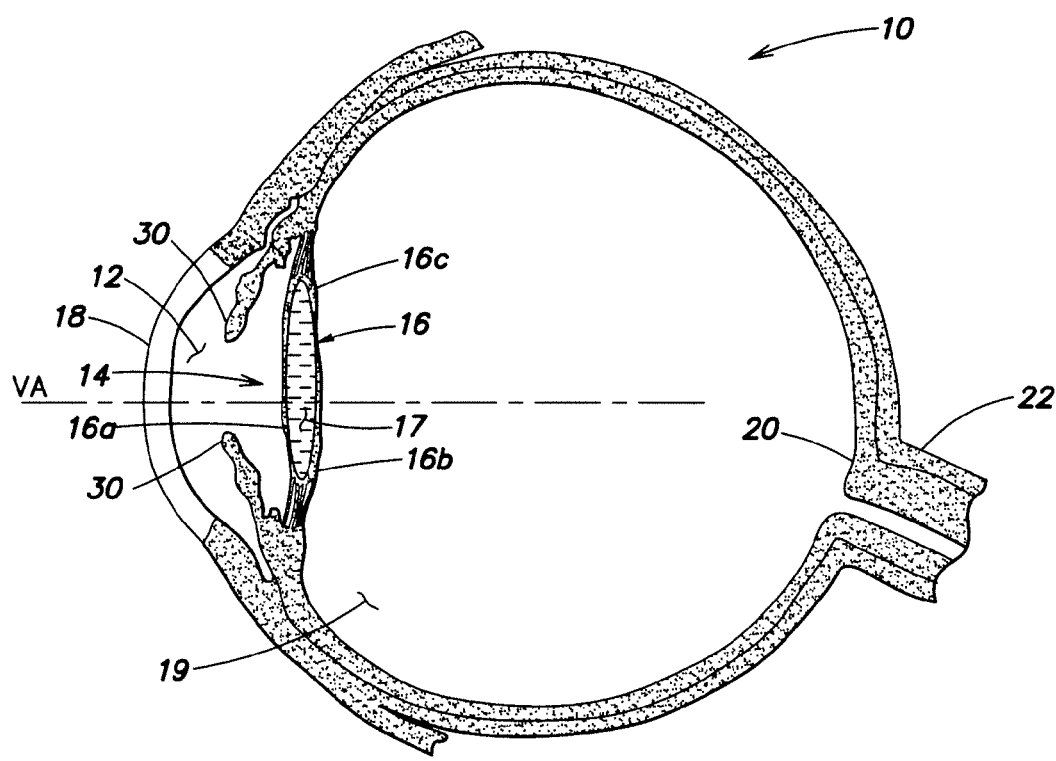
FIG. 1 is a schematic cross-sectional view of a human eye.
Figure 2:
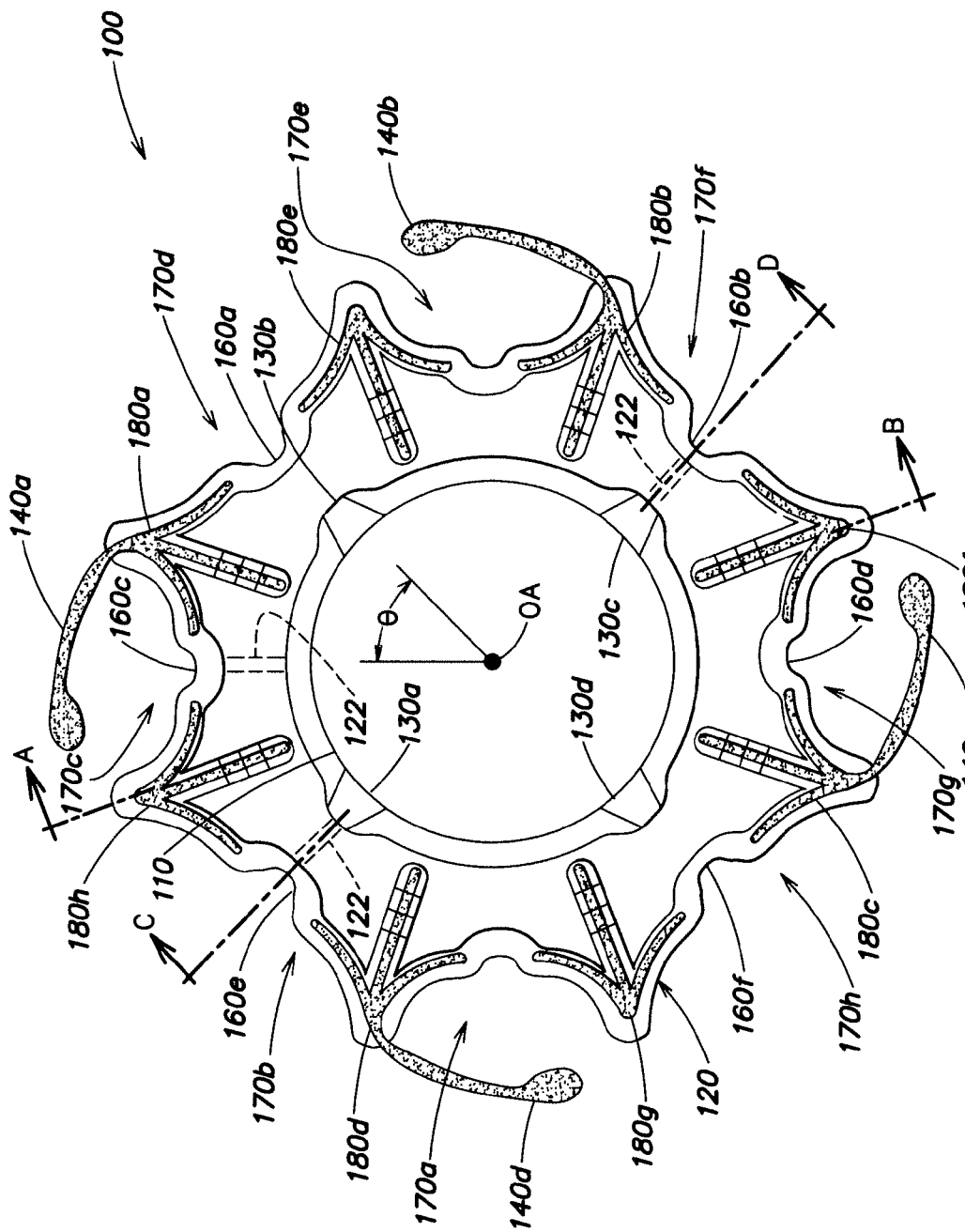
FIG. 2 is a view of an anterior surface of an example of an embodiment of a lens according to aspects of the present invention.

FIG. 2 is a view of an anterior surface of an example of an embodiment of an accommodating intraocular lens 100 according to aspects of the present invention. Lens 100 comprises an optic 110, and a haptic plate 120. The haptic plate is coupled to the optic by at least one connector 130a-130d.

An aspect of the invention is directed to a lens having a haptic plate that surrounds the optic. Additionally, as described in greater detail below, the haptic plate and the optic have a combined surface area that is sufficient to reduce or eliminate the herniation that occurs around conventional lenses during accommodation.

As described below, bulging along portions of the vitreous body contacting the plate is limited thereby causing an increased bulge at the optic. Typically, a lens is selected such that the optic and haptic plate are sized such that they combine to substantially cover the posterior capsule of an eye. Connectors 130a-130d are typically configured to allow translation of the optic relative to the haptic plate in response to such bulging of the vitreous body.

The term "surrounding" as used herein to describe the relationship of the haptic plate relative to the optic refers to bounding on 360-degrees in the plane illustrated in FIG. 2. It will be appreciated that it is typically advantageous that the plate form a continuous surface such that it bounds the optic at all angles (θ) about the optical axis OA and extends over a diameter that is approximately equal to the diameter of the capsular bag into which it is to be placed (i.e., the plate covers the posterior capsule). However, as discussed below, some deviation from such a construction may be tolerable or desirable.

In some embodiments, as illustrated in FIG. 2, the plate forms a continuous 360-degree boundary to enhance the ability to limit bulging of the vitreous body in locations adjacent to the plate. In some such embodiments, the plate is constructed to be rigid throughout the 360 degrees. In such embodiments, it is typically advantageous to avoid the use of a hinge in the plate (i.e., the plate is hingeless).

Although in the illustrated embodiment the plate forms a continuous 360-degree boundary, the ability to limit bulging of the vitreous body in locations adjacent to the plate and thereby increasing bulging at the optic can be achieved without the plate forming a continuous boundary. For instance, one or more interstices 122 (shown in dashed lines) extending from the inner edge of plate 120 to the outer edge of plate 120 or some fraction of said dimension could be included. Accordingly, some embodiments of lenses may have two, three or more haptic plates which, together, surround optic 110 on 360-degrees.

As stated above, the diameter of the haptic plate is selected to cover or substantially cover portions of the posterior capsule that are not covered by the optic so as to limit herniation around the lens. However, some deviation from complete coverage of the posterior capsule by the plate and optic may be tolerable or desirable. For example, in the illustrated embodiment, the outer boundary is scalloped (i.e., the plate has concavities 170a-170h to provide regions of reduced diameter) which the inventor has found desirable to facilitate placement of a lens of a given size into eyes of patients having capsular bags of differing sizes. In such embodiments, the lens will cover a larger portion of the posterior capsule along line A-B than along line C-D.

Typical capsular bag diameters range from 10-13 mm with an average of about 11.5 millimeters (i.e., an area of about 104 mm$^2$). Assuming an optic having a diameter of 5 mm (i.e., an area of about 20 mm$^2$), about 84 mm$^2$ of posterior capsule is not covered by the optic. The Applicant proposes that the area of the one or more haptic plates surrounding the optic have a combined area of at least 60 mm$^2$ (about 70% of the area not covered by the optic) and in some embodiments at least 65 mm$^2$ (about 80% of the area not covered by the optic).

It will be appreciated that, in some embodiments, the optic and haptic plate combine to cover at least 65% of the posterior capsule of an average eye (i.e., the optic and haptic plate have an combined surface area of about 70 mm$^2$), in some embodiments, the optic and haptic plate cover at least cover at least 70% of the posterior capsule of an average eye (i.e., the optic and haptic plate have an combined surface area of about 75 mm$^2$), in some embodiments, the optic and haptic plate cover at least cover at least 75% of the posterior capsule of an average eye (i.e., the optic and haptic plate have an combined surface area of about 80 mm$^2$), and in some embodiments the optic and haptic plate cover at least 80% of the posterior capsule of the posterior capsule of an average eye (i.e., the optic and haptic plate have an combined surface area of about 85 mm$^2$). Typically, the combined surface area of the optic and haptic plate is less than 95% of the posterior capsule of an average eye (i.e., the optic and haptic plate have an combined surface area of about 100 mm$^2$) to permit fitting with eyes having capsular bags of different sizes. Accordingly, the optic and haptic plate have a combined surface area between 70 mm$^2$-100 mm$^2$. In some embodiments, the optic and haptic plate have a combined surface area between 75 mm$^2$-100 mm$^2$. In some embodiments, the optic and haptic plate have a combined surface area between 80 mm$^2$-100 mm$^2$. In some embodiments, the optic and haptic plate have a combined surface area between 90 mm$^2$-10 mm$^2$.

It will be appreciated that for a plate to be effective at covering the posterior capsule, it typically advantageous that it have a substantial width in the radial dimension (i.e., measured in a direction extending perpendicularly from the optical axis OA). In some embodiments, the haptic plate or each haptic plate is selected to have a width in the radial dimension of between 1 mm and 3.5 mm across the haptic plate's entire angular extent (in direction θ) and, in some embodiments the width is at least 1.5-3.5 mm across its entire angular extent (in direction θ). In some embodiments the width is at least 2.0-3.5 mm across its entire angular extent (in direction θ). In some embodiments the width is at least 2.5-3.5 mm across its entire angular extent (in direction θ). The width of the haptic plate or plates may depend in part on the diameter of the optic.

In the illustrated embodiment, the lens has connectors 130a-130d to connect the optic to the haptic plate. It will be appreciated that they are relatively flexible compared to the haptic plate, thereby permitting a large deflection of the optic relative to the deflection of the plate. Although there are four connectors in the illustrated embodiment, one or more connectors may be used to couple the optic to the haptic plate.

In the illustrated embodiment, the haptic plate has filaments 140a-140d extending from its periphery to help in fixing the haptic plate in a capsular bag (e.g., at the rim) in which it is placed. Such fixation may be particularly effective after fibrosis over the filaments occurs. Additionally, due to the presence of a relatively rigid haptic plate, the filaments operate as a capsular tension ring thus adding the integrity of the capsule-zonule structure, and possibly compensating for broken zonules.

For example, the filaments may comprise polyimide. In the illustrated embodiment, four filaments disposed 90 degrees apart from one another are present. Typically, four or more filaments are disposed at regular intervals about the perimeter of the lens.

The optic and haptic plate may be made of any suitable biocompatible material that is foldable yet having a resilience to flex to achieve accommodative movement and return to its original shape. For example the optic and haptic plate may be made of silicone or Collamer® (a collagen and poly-HEMA-based copolymer).

In some embodiments it is advantageous if haptic plate 120 is more rigid than the connectors 130 (i.e., a given force applied to the haptic plate over a given moment arm causes a particular deflection of the haptic plate and, if the same force over the same moment arm is applied to any one of the connectors, the deflection of the connector is larger than the deflection of haptic plate). It will be appreciated that upon exposure to a particular vitreous pressure during the accommodative process, in such embodiments, the plate will remain relatively stationary (due at least in part to plate extending proximate to the capsular rim) and the optic will be caused to move. It will be appreciated that, in embodiments having filaments, after fibrosis over the filaments occurs, the filaments and haptic plate form a rigid structure within the capsular bag thereby promoting vitreous body movement occurring during accommodation to result primarily in movement of the optic. Such a result is due at least in part to the relatively low rigidity of the connectors.

It will also be appreciated that a given volume of vitreous fluid is displaced by contraction of the ciliary muscle. By appropriately controlling the relative rigidity of the plate and the connectors, most of the forward displacement of the vitreous can be caused to occur behind the optic thereby enhancing the accommodative movement of the optic. In some embodiments, the lens is relatively thin (i.e., the edge of the optic is between 50-150 microns) so that, in addition to accommodative translation of the optic as the connectors extend, the optic can be deformed to alter the optical power of the optic.

In some embodiments, implants can be added to increase rigidity of the plate. In the illustrated embodiment, ribs 180a-180h have been added to increase rigidity of the plate. Typically, the rib implants will be of different material than the remainder of the lens body. For example, in the illustrated embodiment, the ribs are made of a polyimide material, the same material used to form haptic filaments. Four of the ribs 180a-180d are attached to a corresponding filament 140, and four of the ribs 180e-180h are separate of the filaments. In some embodiments, the ribs may be extended to connect together at the notches and thereby from a single rib skeleton extending around the entire perimeter of the lens.

Figure 3A:
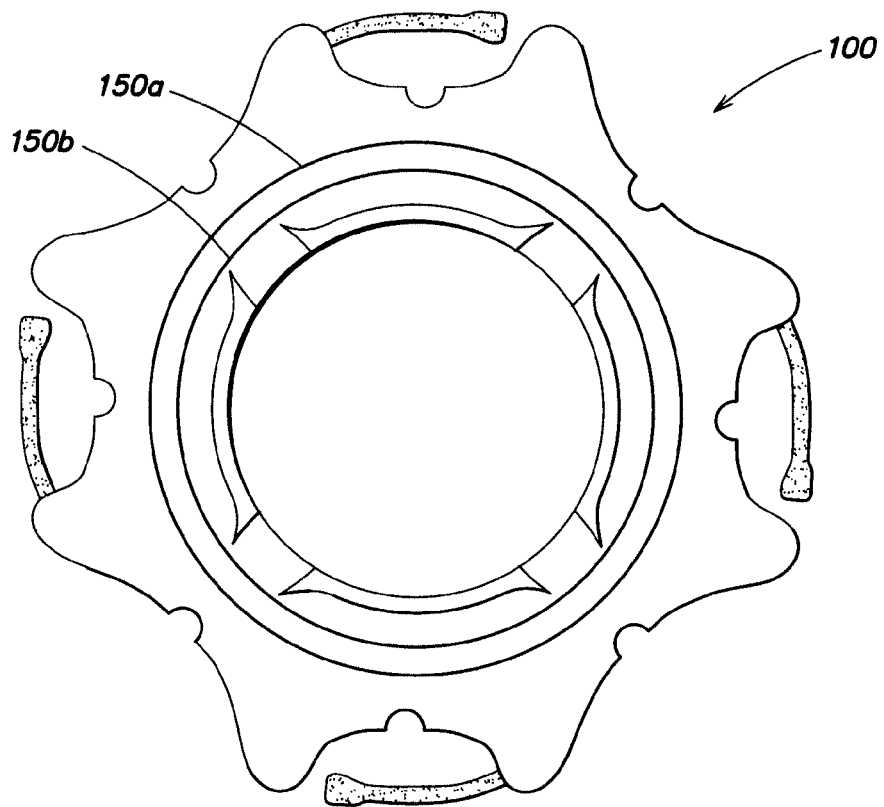
FIG. 3A is a view of a posterior surface of the lens of FIG. 2.

In some embodiments, the rigidity of the plate may be enhanced by appropriately selecting the dimensions of the plate. For example, the plate may have a relatively large thickness compared to at least a portion of the connectors. In some embodiments, the haptic plate has a thickness that is greater than the thickness of any portion of the at least one connector. The increased thickness may occur throughout the entire plate or at selected portions of the plate. For example, the plate may have one or more ridges 150a, 150b (shown in FIG. 3A). In some embodiments, the ridges are 0.1 mm in height and 0.1 mm in width (measured radially across the ridges). It will be appreciated that ridges may be provided with sharp edges disposed on the posterior surface of the lens to prevent posterior capsular opacification (PCO). In some embodiments, the one or more ridges extend 360 degrees around the haptic plate thereby providing 360 degrees of protection from PCO. In some embodiments, a conventional anti-PCO structure (e.g., a sharp edge on the optic) may be provided on the posterior surface.

As an alternative to ridges, one or more troughs with sharp edges may be provided on the posterior surface of the haptic plate to protect from PCO. In such embodiments, it may be advantageous that the haptic plate is constructed to otherwise provide appropriate stiffness to the plate (e.g., using ribs as described above). In some embodiments it is advantageous if the lens has a posterior vault to cause the optic to be biased toward the vitreous body when the lens is located in a capsular bag. In some embodiments, the haptic plate is formed in a conical shape with the optic positioned at the end of the cone having a smaller diameter to further promote movement of the optic by positioning the optic posteriorly.

Although a plate may be constructed to be relatively rigid, it is also desirable that the plate and optic be foldable to facilitate insertion of the lens into an eye. Notches $160a$-$160f$ are provided on the lens body to make the lens predisposed to fold along an axis between notches. For example, the illustrated lens is configured to permit three folds. Each of the sides can be folded (i.e., along an axis between notches $160a$ and $160b$ and along an axis between notches $160e$ and $160f$) and the lens can be folded in half about axis (i.e., along an axis between notches $160c$ and $160d$), each of the folds occurring about an axis extending through opposing notches. Such folding may be used to facilitate loading of a lens into an IOL injector or other inserter.

It will be appreciated that, in some embodiments of lenses according to aspects of the present invention do not have a hinge connecting the optic to the haptic plate (i.e., the lens is hingeless between the haptic plates and the optic). Such a construction facilitates accommodation movement of the optic while maintaining the haptic plate in a relatively fixed location within the capsular bag of the eye. The connectors form tethers (i.e., straps) that permit translation of the optic which occurs due to stretching of the connectors. By suitably constructing the connectors, the connectors can be made to have a relatively low spring constant in response to a tensile force, as compared to the haptic plate, so that stretching of the connectors occurs in response to vitreous pressure. As used herein the term "hinge" refers to a structure that merely allows rotation about a hinge axis. It is to be understood that, although some embodiments comprise straps and no hinges, in some embodiments of lenses according to the present invention, the one or more connectors may comprise one or more straps and/or a hinges.

Although the illustrated lens has four connectors, one or more connectors may be used. For example, a single connector (also referred to as a skirt) may extend 360 degrees around an optic or some portion thereof. In other embodiments, as shown in FIG. 2, the connectors may be configured as straps, each strap having a width that extends a limited distance around the optic. In some embodiments, non-optical portions of the lens, e.g., the plate and the connectors are frosted to avoid glare caused by scattering of light.

Figure 3B:
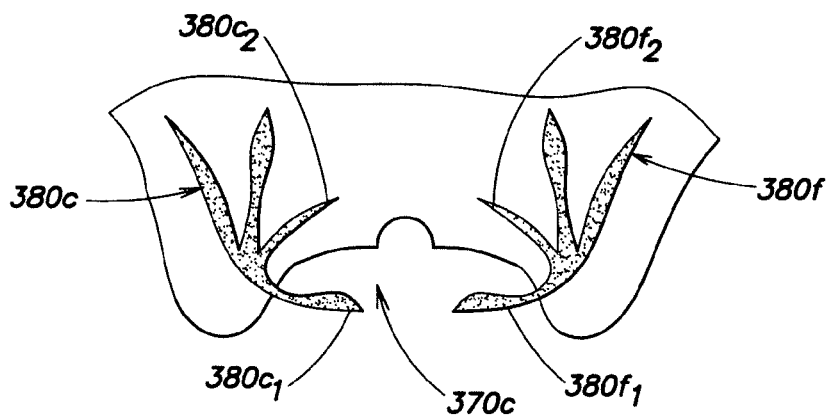
FIG. 3B is a view of an alternative filament structure.

FIG. 3B is a view of an alternative filament structure in which adjacent filaments $380c$ and $380f$ extend toward one another across concavity $370c$. The filaments can have any suitable shape. The ribs of adjacent filament may be attached to one another. For example ribs $380c_1$ and $380f_1$ may be connected together and/or ribs $380c_2$ and $380f_2$ may be connected together.

Although the above description presents a lens sized and shaped to fit into the capsular bag of an eye, in some embodiments, a lens may be sized and shaped to fit in an eye sulcus. It will be appreciated that the accommodative ability of a lens placed in the sulcus will depend in part on the dimensions of an eye (i.e., the space between a lens so placed and the surface vitreous body).

Figure 4:
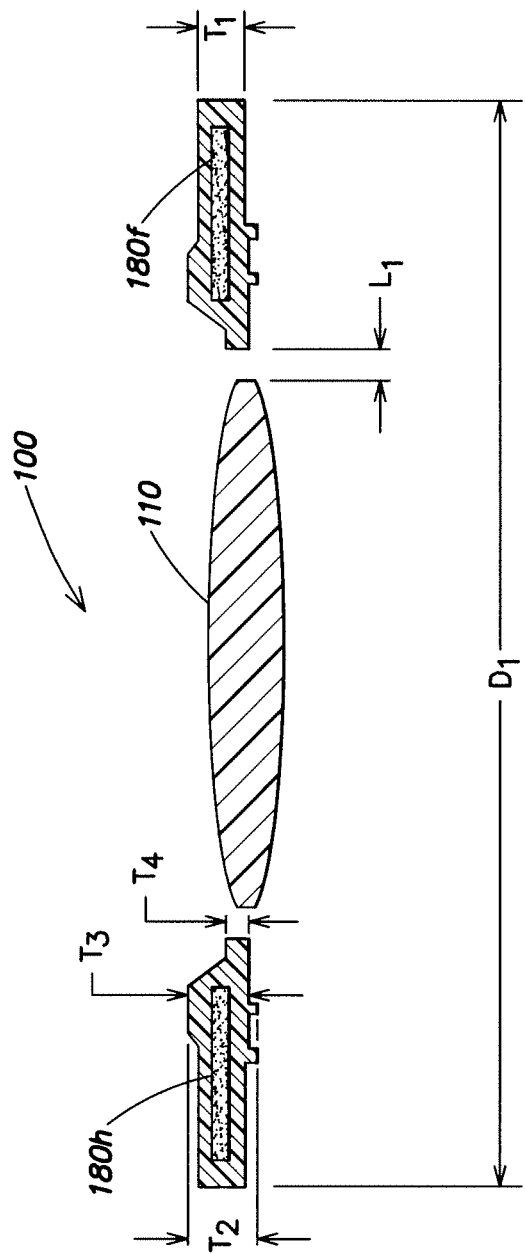
FIG. 4 is a cross section of the lens taken along line A-B of FIG. 2.
Figure 5:
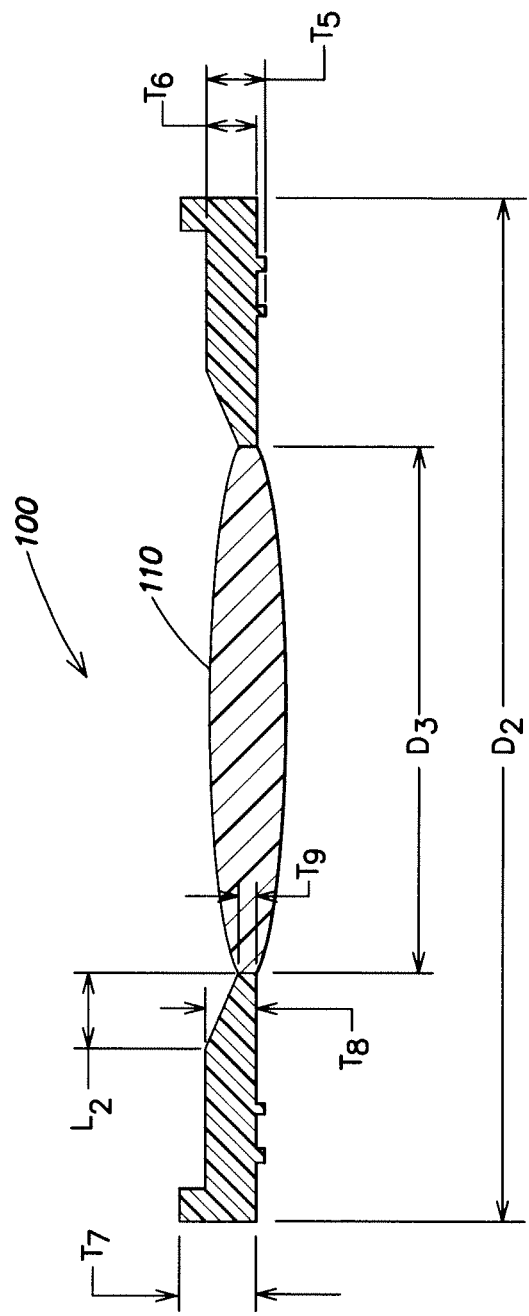
FIG. 5 is a cross section of the lens taken along line C-D of FIG. 2.

Examples of dimensions for lens 100 are provided below with reference to FIGS. 4 and 5.

$T_1$=0.45 mm
$T_2$=0.65 mm
$T_3$=0.55 mm
$T_4$=0.25 mm
$T_5$=0.35 mm
$T_6$=0.25 mm
$T_7$=0.45 mm
$T_8$=0.25 mm
$T_9$=0.10 mm
$D_1$=10.75 mm
$D_2$=9.75 mm
$D_3$=5.0 mm
$L_1$=0.3 mm
$L_2$=0.5 mm

Figure 6C:
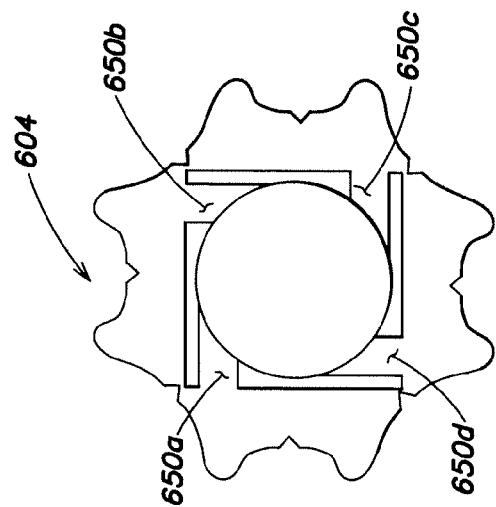
FIGS. 6A-6C are top views of alternative embodiments of lenses each having an alternate connector configuration.
Figure 6B:
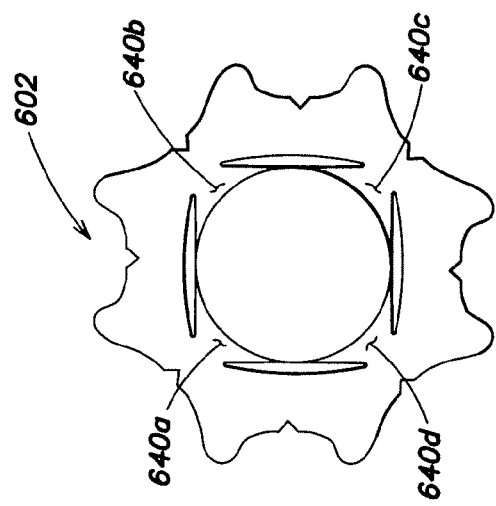
Figure 6A:
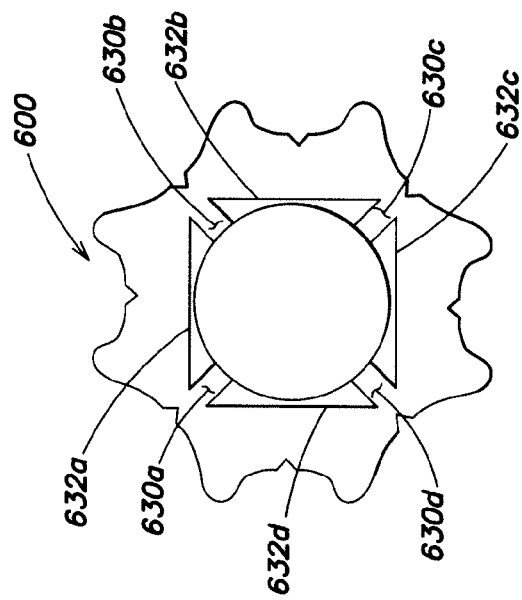

FIGS. 6A-6C are top views of further examples of IOL having different connector constructions. In FIG. 6A, a lens 600 is shown having rectangular connectors $630a$-$630d$ between openings $632a$-$632d$. In FIG. 6B, a lens 602 is shown having tapered connectors $640a$-$640d$ between openings. In FIG. 6C, a lens 604 is shown having tangential connectors $650a$-$650d$ between openings. Although each lens is shown as having four connectors, as stated above, any suitable number of connectors can be used. However, lenses having connector shapes as illustrated in FIGS. 6A-6C will have at least two connectors.

Lenses according to aspects of the present invention may be inserted into an eye using any suitable technique. For example, surgical forceps may be used. Alternatively, an injector comprising an actuation element (e.g., a plunger) may be implemented. A lens may be folded in half, or in thirds as described above or in any other suitable manner. The lumen of the injector may be sloped so as to impart a further folding or compression of the lens as it is injected into an eye.

An aspect of the invention is directed to a method of applying an accommodating intraocular lens (AIOL) constructed as set forth above. The lens is implanted into a subject's eye. The lens is selected such that the at least one haptic plate and optic cover between 65% and 95% of a posterior capsule of the subject's eye. Typically the posterior capsule diameter is in a range from 10-13 mm; however, a subject may have any size eye. In some applications, the at least one haptic plate and optic may cover between 70% and 95% of a posterior capsule of the subject's eye. In some applications, the at least one haptic plate and optic may cover between 75% and 95% of a posterior capsule of the subject's eye. In some applications, the at least one haptic plate and optic may cover between 80% and 95% of a posterior capsule of the subject's eye.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. An accommodating intraocular lens (AIOL) comprising:
   an optic; and
   at least one haptic plate coupled to the optic by at least one connector, the connector being less rigid than the haptic plate, the at least one haptic plate surrounding the optic, and the optic and haptic plate having a combined surface area between 70 mm$^2$ and 100 mm$^2$, and the at least one haptic plate having a surface area of at least 65 mm$^2$;
   wherein the at least one connector couples the haptic plate to the optic at a first location and a second location, the first location and the second location being located on a first diameter of the lens, the at least one connector couples the haptic plate to the optic at a third location and a fourth location, the third location and the fourth location being located on a second diameter of the lens, and the first diameter and the second diameter being perpendicular to one another.

2. The AIOL of claim 1, wherein the at least one connector comprises at least four connectors, a first of the four connectors couples the haptic plate to the optic at the first location, a second of the four connectors couples the haptic plate to the optic at the second location, a third of the four connectors couples the haptic plate to the optic at the third location, and a fourth of the four connectors couples the haptic plate to the optic at the fourth location.

3. An accommodating intraocular lens (AIOL) comprising:
 an optic; and
 at least one haptic plate coupled to the optic by at least one connector, the connector being less rigid than the haptic plate, the at least one haptic plate surrounding the optic;

wherein the at least one haptic plate has a width in a radial dimension of 2.0-3.5 mm across its entire angular extent; and wherein the at least one haptic plate has an area of at least 60 $mm^2$.

4. An accommodating intraocular lens (AIOL) comprising:
 an optic; and
 at least one haptic plate coupled to the optic by at least one connector, the connector being less rigid than the haptic plate, the at least one haptic plate surrounding the optic, and the optic and haptic plate having a combined surface area between 70 $mm^2$ and 100 $mm^2$, and the at least one haptic plate having a surface area of at least 65 $mm^2$;

wherein the at least one connector is configured to permit translation of the optic by stretching of the at least one connector.

\* \* \* \* \*